(12) United States Patent
Hassler et al.

(10) Patent No.: US 7,012,701 B2
(45) Date of Patent: Mar. 14, 2006

(54) MEASURING FOR DEVICE FOR CONTACTLESS MEASUREMENT OF TIRES

(75) Inventors: Ulf Hassler, Heilsbronn (DE); Peter Schmitt, Erlangen (DE); Günther Kostka, Erlangen (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 336 days.

(21) Appl. No.: 10/450,595

(22) PCT Filed: Dec. 5, 2001

(86) PCT No.: PCT/EP01/14292

§ 371 (c)(1),
(2), (4) Date: Nov. 3, 2003

(87) PCT Pub. No.: WO02/48648

PCT Pub. Date: Jun. 20, 2002

(65) Prior Publication Data

US 2005/0259859 A1    Nov. 24, 2005

(51) Int. Cl.
*G01B 11/24* (2006.01)
(52) U.S. Cl. .......................... 356/601; 356/602
(58) Field of Classification Search ........... 356/601, 356/237.2
See application file for complete search history.

(56) References Cited

U.S. PATENT DOCUMENTS 6,539,789 B1 * 4/2003 Kostka et al. ............... 73/146

FOREIGN PATENT DOCUMENTS

DE    38 27 696 C2    8/1988
DE    198 49 793 C1    10/1998

* cited by examiner

*Primary Examiner*—Gregory J. Toatley, Jr.
*Assistant Examiner*—Roy M. Punnoose
(74) *Attorney, Agent, or Firm*—Thomas, Kayden, Horstemeyer & Risley

(57) ABSTRACT

In a method for characterizing a surface comprising a localized unevenness, a contour line of the surface is initially created as a function of a location variable. Subsequently, the localized unevenness is detected in the contour line and eliminated from the contour line, so that an incomplete contour line results as a function of the location variable, which characterizes the surface without the localized unevenness. The incomplete contour line may be used to either be able to evaluate the surface without any localized points of unevenness, for example to determine the side wobble or height wobble of a tire, if the surface is a side flank and/or a running tread of a vehicle tire, or to classify the localized points of unevenness without any influence of the surface.

16 Claims, 7 Drawing Sheets

MEASURING FOR DEVICE FOR CONTACTLESS MEASUREMENT OF TIRES

FIELD OF THE INVENTION

The present invention relates to industrial quality control performed on products with surfaces comprising low-scale structuring with regard to verification for defects of fabrication, and in particular to methods and apparatus for characterizing a surface, for determining a shape anomaly of a surface, and for characterizing localized unevenness on a surface.

BACKGROUND OF THE INVENTION AND PRIOR ART

In industrial quality control performed on products with surfaces comprising low-scale structuring (relief-like surfaces) with regard to verification for defects of fabrication reflected by a specific anomaly of the shaping of the surface, contactless real-time measuring methods may be employed. Particularly in characterizing vehicle tires with regard to side or height wobble it is essential to recognize bulges or constrictions, on the one hand, and inscriptions and/or markings applied to the tires, on the other hand, so that they do not interfere with characterizing the vehicle tire.

The particular difficulty in detecting side or height wobble is the fact that raised, relief-like graphic characters or markings have been applied, as a rule simultaneously, on the areas to be tested, and that the anomaly structure is situated at the same height interval as the writing or at a higher height interval than same, it being possible that the tire surface to be tested additionally has a torus-shaped curvature. As a consequence, correct measuring of the anomaly of height is distorted or, in many cases, even-prevented by the presence of the structures of writing.

The production of vehicle tires may give rise to defects of fabrication in the inner structure which significantly influence the mechanical properties and therefore the operating behavior. It is necessary to discard any such products. In vehicle tires, such production defects may occur on the side faces or running treads, and typically become apparent in the form of deviations from a radially symmetric surface. The extensions of such imperfections are generally higher than the constructive structures which are present on the surface at the same time, such as relieves of writing or marking.

So far, mainly capacitive measuring methods have been employed for this test assignment in the field of industry, which, however, can only provide insufficient testing depths for the reasons laid down below. While the surface is moving, i.e. while the tire is rotating, a change in the distance between the measuring electrode and the tire surface is determined by means of a change in the capacity of a measuring sensor. The disadvantage is its relatively coarse lateral spatial resolution due to its geometry, which implies that only a small number of tracks per width of the testing range may be suitable for testing. The measurement signal contains no sufficient information on the precise course of a deflection in height, so that any short-range structures (relief of writing) cannot be recognized and blanked out for further calculation.

In addition, certain tire manufacturers employ tactile (contacting) measuring methods, which, however, place certain requirements upon the geometry of the objects to be measured. The limitation is that on the surface to be examined, an explicit track to be measured must be provided which must not comprise any constructive structures, and the minimum width of which must include the geometry of the measuring sensor and potential irregularities in the concentricity during measuring. Under these circumstances, the measuring method is capable of determining relatively reliable measuring values. However, due to the geometric limitations and the current tendency, conflicting therewith, to produce very narrow tire side flanks (tires with a small cross-section), it does not provide a satisfactory measuring method for general use.

A known method for measuring surface contours is optical triangulation. It includes focusing a light beam (generally a laser beam) onto the surface to be measured, and optically imaging the diffusely reflected radiation onto a sensor with a plurality of picture elements (pixels). If the geometry between the camera and the light beam remains unchanged, the change in the spatial position of the light intersection point on the object to be measured along the beam may be determined from a shift of the point of light reflected on the sensor area. Such a measurement is initially performed point by point. If a whole region is to be tested, the object under test is moved along beneath the triangulator measuring arrangement, and the measuring values are recorded in a fast sequence, so that a narrow, annular track on the tire side face is detected.

With the increasing availability of high-performance laser light sources and optical sensors, bulge testing systems on the basis on laser triangulation have recently been offered. These systems are capable of capturing a specific track to be measured on the tire surface at a high spatial resolution, and to evaluate same with regard to potential shape anomalies. However, since these methods are not able to reliably recognize constructive structures of writing, the height of the shape anomalies is distorted by the height of the regular structures of writing. This is added to by the problem that the maximum amplitude of any occurring shape anomalies is not necessarily situated on the selected track to be measured.

A derivative of the described triangulation which is also known includes sampling the surface by means of fan beam and area sensor (light section method). The height-related information may be determined along the measuring line on the surface by means of the light stroke projected onto the sensor (line of intersection between the fan beam and the object surface). By moving the object, the height-related information along this line is recorded row by row and subsequently combined to form a complete 2D height image comprising the respective height-related information in each image point. With sufficient resolution of the measurement in terms of space and time, the data set thus produced contains the height-related information derived from an entire surface region, including the structures of defects and writing and/or marking. However, since structures of writing and defects are situated in the same range of height, and since these structures are situated on a surface which is strongly curved in relation to these structures, it is not possible—even by means of the height images thus acquired—to achieve accurate measuring of the surface in a simple manner without special data processing methods when suppressing the relief structures.

WO 00/25088 discloses methods and apparatus for determining points of unevenness in a domed surface, such as a tire side wall, using band-pass filtering. In particular, a three-dimensional surface representation of the tire side wall is created. Hereupon, the doming is extracted from the three-dimensional representation of the surface, and the edges of the structuring, such as of a writing or of markings, are smoothened to obtain a domeless representation of the domed surface. The surface now contains the potential unevenness, such as a constriction or a bulge on the tire side wall, but the edges of the inscription are now smoothened. Subsequently, the domeless representation is compared to a threshold so as to determine two-dimensional regions of the domeless representation which have a predetermined relation to the threshold value. Eventually, the areas of the areas determined are evaluated, wherein an region is detected to be an unevenness if its surface area is larger than a predetermined surface area. The relief-like structures of writing on the tires no longer play a role in evaluating the areas, since the edges of these inscriptions have been smoothened, and thus the heights of the inscriptions have been reduced such that they no longer exceed the threshold value at all, or such that they now have only a small area exceeding the threshold value. In the evaluation of the size of the areas exceeding the threshold value, these small areas may readily be distinguished from those areas which are due to bulges or constrictions. For extracting the surface and for smoothing the edges, a band pass filter is preferably used which has an upper and a lower cut-off frequency, the lower cut-off frequency being set such that the doming is suppressed, and wherein the upper cut-off frequency is set such that the edges are smoothened, whereas the points of unevenness in the form of bulges or constrictions substantially are not adversely affected.

Even though this method is capable of reliably distinguishing bulges and/or constrictions from inscriptions on the tire side wall, it cannot be employed for ascertaining a side wobble of a tire or for ascertaining a height wobble of a tire, since the structures of writing undergo low-pass filtering, which in turn means that averaging is performed on the structures of writing existing on the tires. Therefore, excessive height values are created wherever there are inscriptions on the tire, which is a problem particularly if the writing is not evenly distributed across the periphery of the tire. Thus, after low-pass filtering of the three-dimensional surface representation, the "remainder" of an inscription might suggest a side wobble even though there is no such side wobble at all.

Specifically in tire manufacturing, however, there is the requirement that only those tires are discarded in a quality check which actually have such a pronounced side wobble that same exceeds a limit, such a limit typically being defined by the purchasers of the tires, such as, for example, the automotive industry. If tires which are erroneously believed to have a side wobble due to the structures of writing they bear are discarded, this means that tires which are actually fine are discarded, which, with regard to the total cost, leads to an increase in the cost per tire.

Alternatively, tires which have been discarded could once again be manually examined for side wobble to find out whether they indeed have excessive side wobble, or whether they have just been the subject of misjudgment. If such a two-step discarding method is performed, this again creates additional costs, which again leads to a tire becoming more expensive.

SUMMARY OF THE INVENTION

The object of the present invention is to provide a safe concept for characterizing a surface which may comprise a localized unevenness.

In accordance with a first aspect of the invention, this object is achieved by a method for characterizing a surface having a localized unevenness, comprising: creating a plurality of adjacent contour lines of the surface to create a two-dimensional height representation of the surface, a contour line of the surface being created as a function of a location variable; detecting the localized unevenness in the two-dimensional height representation, wherein the step of detecting comprises: creating a variation representation from the height representation, detecting localized points of unevenness delimited by edges using a variation threshold, and detecting essentially edge-free localized points of unevenness using the variation threshold; and eliminating the detected points of unevenness delimited by edges and the detected essentially edge-free points of unevenness from the height representation, so that an incomplete representation of the surface results which characterizes the surface without the localized unevenness.

In accordance with a second aspect of the invention, this object is achieved by a method for determining a shape anomaly of a surface having a localized unevenness which is not to be determined as a shape anomaly, comprising: characterizing the surface to obtain an incomplete height representation which comprises merely information relating to the shape anomaly, but no information relating to the localized unevenness, the step of characterizing including: creating a plurality of adjacent contour lines of the surface to create a two-dimensional height representation of the surface, a contour line of the surface being created as a function of a location variable; detecting the localized unevenness in the two-dimensional height representation, wherein the step of detecting comprises: creating a variation representation from the height representation, detecting localized points of unevenness delimited by edges using a variation threshold, and detecting essentially edge-free localized points of unevenness using the variation threshold; eliminating the detected points of unevenness delimited by edges and the detected essentially edge-free points of unevenness from the height representation, so that an incomplete representation of the surface results which characterizes the surface without the localized unevenness; adjusting an analytical function to the incomplete surface; comparing a maximum of the analytical function to a predetermined threshold value; and determining a shape anomaly if the maximum exceeds the threshold value.

In accordance with a third aspect of the invention, this object is achieved by a method for characterizing a localized unevenness on a surface, comprising: characterizing the surface to obtain an incomplete representation of the surface comprising merely information relating to the shape anomaly, but no information relating to the localized unevenness, the step of characterizing including the following steps: creating a plurality of adjacent contour lines of the surface to create a two-dimensional height representation of the surface, a contour line of the surface being created as a function of a location variable; detecting the localized unevenness in the two-dimensional height representation, wherein the step of detecting comprises: creating a variation representation from the height representation, detecting localized points of unevenness delimited by edges using a variation threshold, detecting essentially edge-free localized points of unevenness using the variation threshold; and eliminating the detected points of unevenness delimited by edges and the detected essentially edge-free points of unevenness from the height representation, so that an incomplete representation of the surface results which characterizes the surface without the localized unevenness; filling up the incomplete representation using the values of the incomplete representation to obtain a filled-up representation; subtracting the filled-up representation from the original representation to obtain a representation of unevenness including merely information relating to the localized unevenness; classifying the unevenness on the basis of its extension, height and/or geometrical shape.

In accordance with a fourth aspect of the invention, this object is achieved by an apparatus for characterizing a surface having a localized unevenness, comprising: means for creating a plurality of adjacent contour lines of the surface to create a two-dimensional height representation of the surface, a contour line of the surface being created as a function of a location variable; means for detecting the localized unevenness in the two-dimensional height representation, the means for detecting being operative for: creating a variation representation from the height representation, detecting localized points of unevenness delimited by edges using a variation threshold, and detecting essentially edge-free localized points of unevenness using the variation threshold; and means for eliminating the detected points of unevenness delimited by edges and the detected essentially edge-free points of unevenness from the height representation, so that an incomplete representation of the surface results which characterizes the surface without the localized unevenness.

In accordance with a fifth aspect of the invention, this object is achieved by an apparatus for determining a shape anomaly of a surface having a localized unevenness which is not to be determined as a shape anomaly, comprising: means for characterizing the surface to obtain an incomplete representation of the surface comprising merely information relating to the shape anomaly, but no information relating to the localized unevenness, the means of characterizing being operative for: creating a plurality of adjacent contour lines of the surface to create a two-dimensional height representation of the surface, a contour line of the surface being created as a function of a location variable; detecting the localized unevenness in the two-dimensional height representation, wherein the step of detecting comprises: creating a variation representation from the height representation, detecting localized points of unevenness delimited by edges using a variation threshold, detecting essentially edge-free localized points of unevenness using the variation threshold; and eliminating the detected points of unevenness delimited by edges and the detected essentially edge-free points of unevenness from the height representation, so that an incomplete representation of the surface results which characterizes the surface without the localized unevenness; means for adjusting an analytical function to the incomplete surface; means for comparing a maximum of the analytical function to a predetermined threshold value; means for determining a shape anomaly if the maximum exceeds the threshold value.

In accordance with a sixth aspect of the invention, this object is achieved by an apparatus for characterizing a localized unevenness on a surface, comprising: means for characterizing the surface to obtain an incomplete representation of the surface comprising merely information relating to the shape anomaly, but no information relating to the localized unevenness, the means of characterizing being operative for: creating a plurality of adjacent contour lines of the surface to create a two-dimensional height representation of the surface, a contour line of the surface being created as a function of a location variable; detecting the localized unevenness in the two-dimensional height representation, wherein the step of detecting comprises: creating a variation representation from the height representation, detecting localized points of unevenness delimited by edges using a variation threshold, detecting essentially edge-free localized points of unevenness using the variation threshold; and eliminating the detected points of unevenness delimited by edges and the detected essentially edge-free points of unevenness from the height representation, so that an incomplete representation of the surface results which characterizes the surface without the localized unevenness; means for filling up the incomplete representation using the values of the incomplete representation to obtain a filled-up contour line; means for subtracting the filled-up representation from the original representation to obtain a line of points of unevenness including merely information relating to the localized unevenness; means for classifying the unevenness on the basis of its extension, height and/or geometrical shape.

The present invention is based on the findings that for characterizing a surface comprising a localized unevenness, this localized unevenness must be detected and eliminated from a representation of the surface to obtain an incomplete surface representation characterizing the surface without the localized unevenness. To this end, a contour line of the surface as a function of a location variable is initially captured. Then a deviation in height in the contour line due to the localized unevenness is detected, whereupon the height deviation detected is finally eliminated from the contour line, so that an incomplete contour line as a function of the location variable results which characterizes the surface without the localized unevenness. If this method is performed for a plurality of contour lines situated side by side, this gradually produces a three-dimensional representation of the surface which, however, is no longer adversely affected by localized points of unevenness. When looking at the example of the tires, the three-dimensional representation of the tire side wall which has been obtained represents the actual shape of the tire without bulges and/or constrictions or inscriptions as examples for localized points of unevenness. By means of this incomplete representation, it may now be readily determined whether the tire has a side wobble, without this determination now being affected by inscriptions, bulges and/or constrictions, since same have been eliminated.

It shall be pointed out that the inventive concept is preferably carried out not only one-dimensionally, but two-dimensionally, whereby the accuracy of detection may be increased significantly. To this end, several contour lines/tracks of the tire which are situated side by side are captured and subsequently evaluated together by evaluating and/or examining two-dimensional regions rather than one-dimensional stretches, as in the general one-dimensional case, with a view to their height/area/environment/position etc. Then, the height of a point of a two-dimensional representation is the third dimension, as it were.

The incomplete representation of the three-dimensional surface may be employed in various ways for examining the surface.

For example, if the side wobble of the tire is to be characterized, an analytical function may be fitted to an incomplete contour line representation of the three-dimensional surface, the amplitude of the fitting function obtained providing a quantitative measure for the side wobble of the tire.

Alternatively, the empty spaces may, for example, simply be filled up by a linear or a cubic interpolation or an interpolation of another kind, so that an ideal representation of the tire without inscription and constriction and/or bulge, that is to say without localized points of unevenness, is obtained.

This ideal representation may then be subtracted from a two-dimensional image of the tire with localized points of unevenness, so that, without band-pass filtering and the like, merely a record of the localized points of unevenness results which is no longer adversely affected by the doming of the tire.

Thus, it is possible to decide, due to the localized points of unevenness, by means of simple algorithms whether what has been detected are inscriptions or bulges and/or constrictions, so as to be able to discard a tire if it exhibits, for example, bulges and/or constrictions which are too pronounced.

If the height wobble of a tire is to be determined, a height representation of the running tread is captured. The incomplete height representation of the running tread then consists in a running tread representation wherein the notches in profile are eliminated, so that it may readily be determined, on the basis of the incomplete height representation, whether the tire exhibits a height wobble, that is to say an ellipsoidal shape or the like, as it were, or whether it exhibits no height wobble, that is to say it comprises an ideal cylinder shape.

Generally, the inventive concept providing a representation and/or characterization of a surface which comprises no more localized points of unevenness may be employed whenever the surface per se, that is to say without the localized points of unevenness, is to be characterized, or whenever the localized points of unevenness without the influence of the surface itself are to be characterized.

BRIEF DESCRIPTION OF THE DRAWINGS

Preferred embodiments of the present invention will be explained below in detail with reference to the accompanying figures, in which.

DETAILED DESCRIPTION OF PREFERRED EMBODIMENTS

Figure 1:
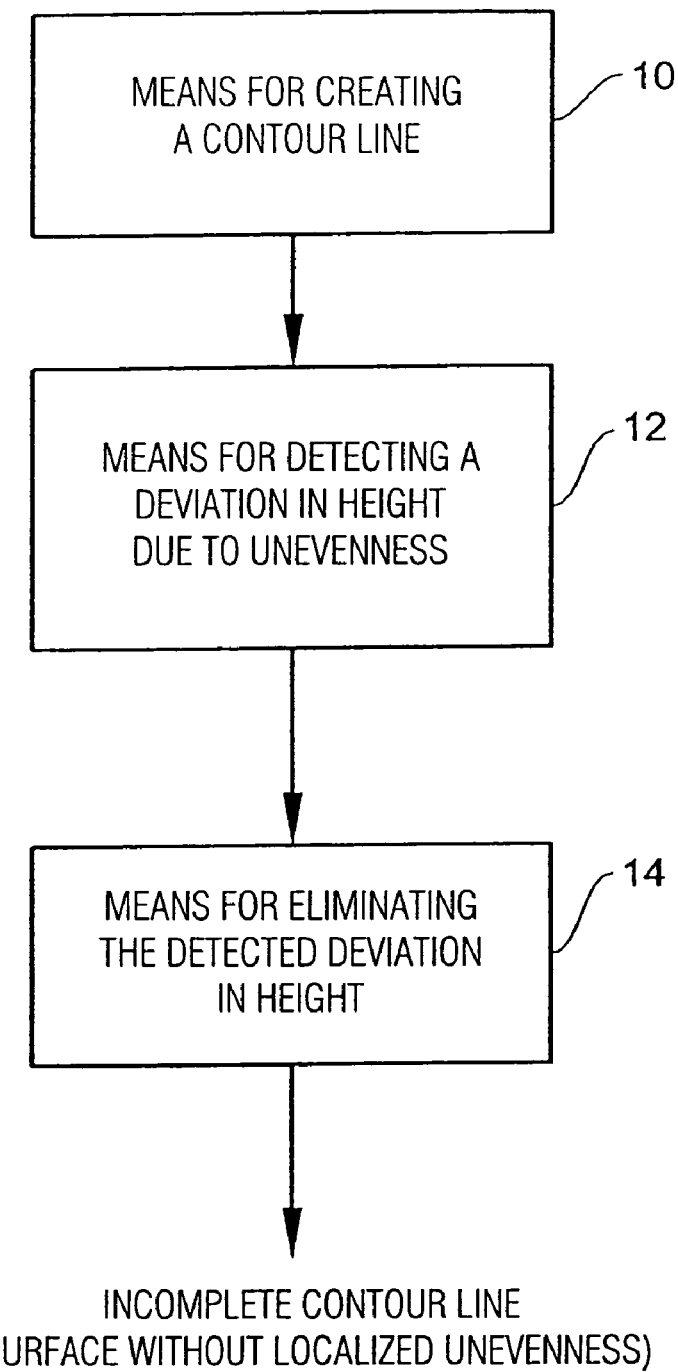
FIG. 1 is a block-diagram representation of the inventive apparatus for characterizing a surface.

An apparatus for characterizing a surface comprising a localized unevenness will be described below with reference to FIG. 1. When looking at a tire side face, the localized unevenness may be, for example, an inscription on the tire, a test structure, or a bulge or constriction in the tire. Initially, such a contour line of the tire side flank is captured by means of optical or capacitive methods using means 10 for creating a contour line. In this context, reference shall be made to FIG. 2.

Figure 2:
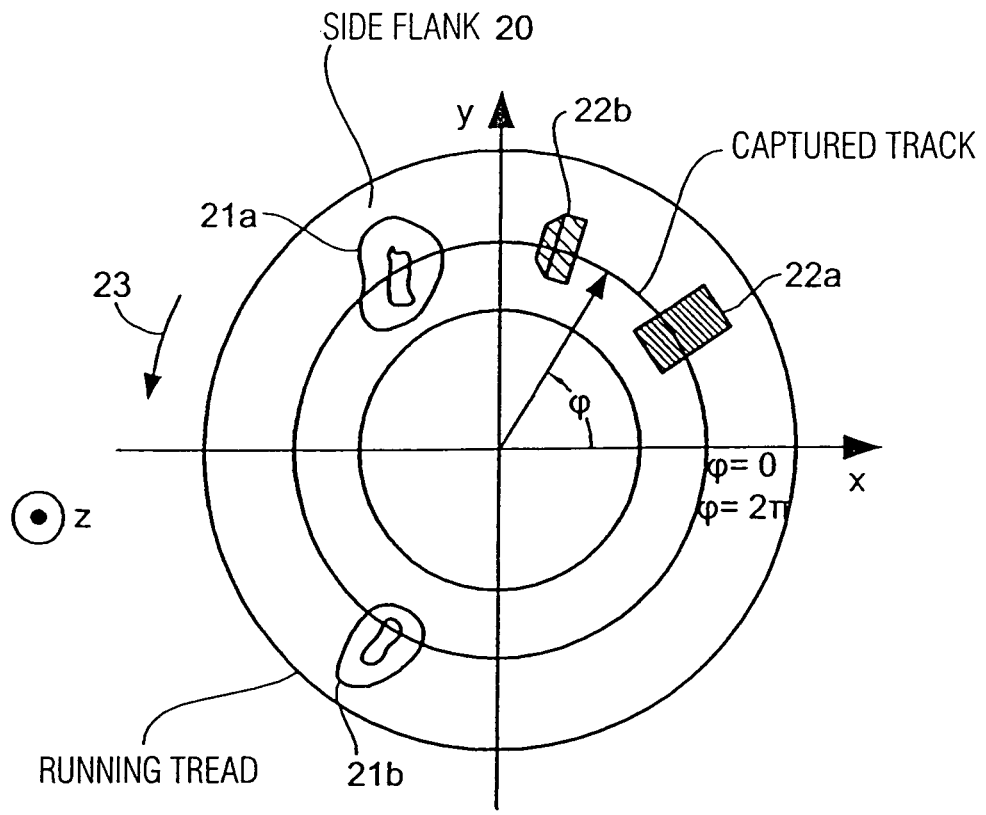
FIG. 2 is a top view of a tire side flank with localized points of unevenness and with a captured track.
Figure 3:
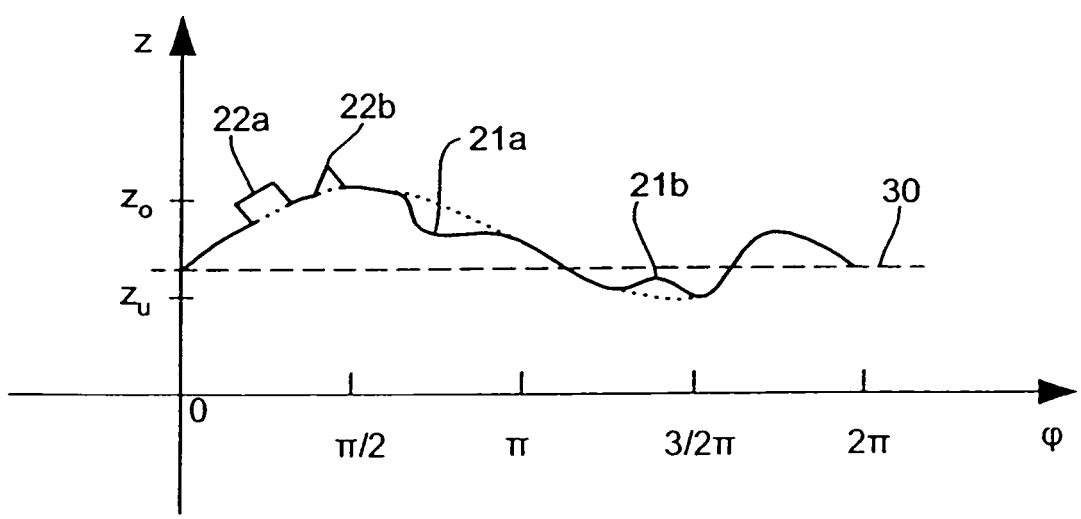
FIG. 3 shows a contour line which might result from recording the track of FIG. 2.

FIG. 2 shows a top view of a tire situated in the xy plane. The tire includes a side flank 20, on which localized points of unevenness are present, such as a bulge or constriction 21a, 21b, or a relief-like localized unevenness 22a, 22b. If the tire is rotated around the origin of the xy coordinate system, as is represented by an arrow 23, and if a fast sequence of individual images are captured, during the rotation of the tire, by means of a sensor (not shown in FIG. 2) mounted above the side flank 20, a contour line of the tire as is represented in FIG. 3 will result. The contour line of the tire initially includes the two edge-like inscriptions as well as the constriction 21a and the bulge 21b. The contour line starts at a location variable 0 and ends at a location variable $2\phi$, the z value, i.e. the height of the contour line, having the same value at the location variable 0 and at the location variable $2\phi$, as the tire has completed one revolution by then.

FIG. 3 represents a tire having a pronounced side wobble, to be precise a maximum side wobble in the positive direction, represented by $z_o$, and a maximum side wobble in the downward direction, represented by $z_u$. If the tire had no side wobble, the contour line would have to correspond exactly to the straight dashed line designated by reference numeral 30 in FIG. 3, apart from the bulges, constrictions and inscriptions.

If the contour line represented in FIG. 2 underwent band-pass filtering by means of the concept represented in WO 00/25088, this would result in an incorrect representation of the side wobble, since the maximum positive side wobble, i.e. the value $z_o$, would be increased by the marking 22b, whereas the downward side wobble $z_u$ would, due to the bulge 21b, be represented in a manner understating its real existence.

In accordance with the invention, means 12 for detecting a height deviation due to a localized unevenness (FIG. 1) are therefore provided. This detection of the bulges and/or points of unevenness 21a, 21b (FIG. 3) may be accomplished, for example, by means of the method described in WO 00/25088. Detection of the inscriptions 22a, 22b, that is to say of the relief-like structures with pronounced edges, could be accomplished, for example, by means of a gradient method which recognizes regions delimited by high positive/negative inclinations.

Alternatively, if the surface to be examined is a generally flat surface, a height threshold might be provided. If the inventive method for characterizing the surface is employed, however, for determining a side wobble and/or a height wobble of a tire, it is preferred to detect the edge-like relief structures by means of a gradient method and to detect the bulges and/or constrictions by means of the known method described in WO 00/25088.

Eventually the contour line represented in FIG. 3 is processed by means 14 for eliminating the detected height deviation by eliminating the detected height deviations. This results in an incomplete contour line which is represented in FIG. 4 for the example shown in FIG. 3.

Figure 4:
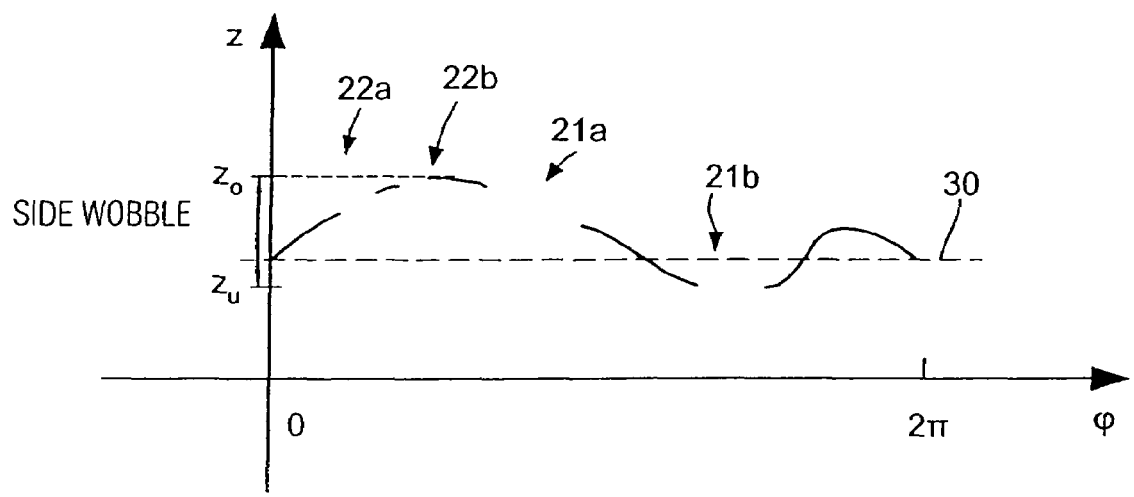
FIG. 4 shows an incomplete contour line after a detection due to of the localized points of unevenness in the contour line.

The incomplete contour line represented in FIG. 4 now represents the surface, but without any localized points of unevenness. This incomplete contour line now may be used for widely varied applications, as will be explained below, to either determine a shape anomaly of the surface, wherein the localized points of unevenness are of no interest, or to eliminate the general "fundamental course" of the surface so as to classify the localized points of unevenness per se.

Before reference is made to FIGS. 5 and 6, which refer to how the incomplete contour line of a tire surface may be used either for ascertaining a side wobble or height wobble, or for differentiating between bulges and inscriptions, a description will be given, using the preferred optical triangulometric principle, of the recording of the contour line, which is achieved by means 10 of FIG. 1.

Here, a light fan beam (laser with specific aspherical refractive optics, 30 mW) is initially directed at the surface to be examined. The diffusely reflected radiation is projected onto a sensor face via a suitable lens system. The shape of the surface irradiated is calculated from the known geometry of the measuring arrangement from the position of the projected line on the sensor face.

The geometry of the arrangement of the light fan beam and the measuring camera as well as the pixel resolution of the camera determine the spatial resolution of the measurement in the lateral and vertical directions. The geometry is selected such that the tire region to be examined is imaged onto the sensor, i.e. a measuring region of 5 cm in the radial direction with a resolution of 0.5 mm, and such that a sufficient height resolution of about 75 μm is achieved at the same time in order to represent the structures of defects, which occur in a range of height >=0.55 mm, in a sufficiently accurate manner.

The spatial resolution of the measurement in the tangential direction is dependent on the image repetition rate of the image camera. The tangential spatial resolution is 1 mm. A tire must be tested within 1 sec. With an assumed diameter of the testing region of, for example, 60 cm, this results in a measuring rate of 1,900 Hz. Sensors specifically suitable for this test problem are manufactured by IVP (type MAPP 2500 PCI). By means of a programmable computer architecture integrated on the sensor chip, a column-by-column determination of the height-related information is performed, so that per sensor image captured, it is only the evaluation result that must be transmitted to the measuring computer in the form of a line.

The light source/camera arrangement which may be employed for the present invention may be the same, for example, as has been described in WO 00/25088. A suitable camera typically has a dust-proof housing, the measuring windows being kept free from dust by means of air cleaning. The height measuring region, which may be realized with such a light source/camera arrangement, in the z direction is 39 mm. The height resolution is 75 μm. The width of the measuring region on the tire flank is, for example, 80 mm.

The height-related information obtained is loaded into a digital data processing system, which may be, for example, a common-use PC, having a display and an operating function, and which has a number of image processing operations performed on it, to achieve detection and blanking-out of both the structures of writing and marking and the short-range points of unevenness. In particular in tire measurement, a possibly torus-shaped curvature of the surface must be taken into account which must not lead to mismeasurement. It is preferred to limit the calculating time to a maximum of 1 sec., so that real-time measurement of tires is possible. This is why it is essential to use of image processing algorithms which are not very expensive in terms of calculating times.

In a one-dimensional embodiment of the present invention, detection and elimination of unperturbed image points, wherein it was not possible to determine any height-related information for reasons of capturing technology, are performed immediately after creating a contour line. Subsequently, a gradient calculation and subsequent threshold value decisions are performed for detecting the relief structures on the tire. In this preferred embodiment, if the amount of the gradient exceeds a certain value, elimination is activated immediately from this value of the location variable. Elimination is performed of an region so long until the gradient again reaches a value above a preset threshold value, however with the sign of the gradient reversed. If an inscription rectangular in cross section, for example the inscription 22a of FIG. 3, is to be eliminated, the gradient of the contour line will have a high positive inclination value immediately at the beginning of the inscription, which inclination value will then fall back to zero at the plateau of the inscription, and then will have a high negative value at the end of the inscription, that is to say at the second edge of the inscription, so as to fall back down to a value near zero once the inscription has been passed. The range of the location variable, which is between the high positive and the high negative gradients, will then be blanked out. If the tire includes negative reliefs, that is to say edge-like recesses, the first gradient, at which the blanking-out is activated, will be a high negative gradient, whereas that point of the location variable at which the blanking-out is deactivated, will have a high positive gradient.

It shall be pointed out that instead of the gradient, the variation may also be used. The term "gradient" refers to a vector, the amount of which equals the inclination value, and the direction of which equals the direction of the inclination. The term "variation", in contrast, includes merely the amount of the gradient vector, is therefore a scalable value and is calculated, for example, from the sum of the difference squares of adjacent image points. For the purposes of the present application, the term "variation" is to be understood such that it also includes a gradient and, in particular, any value indicating a difference in height between adjacent pixels. The variation of a pixel is calculated, for example, from the sum of the difference squares between the pixel under consideration, for which the variation is calculated, and all of the adjacent pixels, e.g. eight adjacent pixels. Of course, other calculation methods are also feasible, such as considering less than eight, for example four, adjacent pixels, etc. The variation only needs to indicate somehow whether a change in height from one pixel to another pixel exists. The variation may therefore be calculated both in a one-dimensional and in a two-dimensional manner. The difference is merely that in the two-dimensional case, not only two neighboring pixels exist, but four or eight neighboring pixels.

For detecting the bulges and/or constrictions 21a, 21b, it is preferred to employ the method described in WO 00/25088, wherein the area of a bulge and/or constriction is determined, whereupon a determination is made, by means of the area of the bulge and/or constriction, or—in the one-dimensional case, when only one track is captured—by means of the length, whether or not what is being dealt with is a bulge which is to be considered.

In accordance with the invention, all regions with relief structures and/or bulges/constrictions are excluded from further calculation, for example to obtain the side wobble of the tire, as is outlined in the incomplete contour lines of FIG. 4.

In the following, reference will be made to FIG. 5 to represent an inventive apparatus for characterizing a surface with regard to a shape anomaly of the surface. To this end, the incomplete contour line of a tire is determined using means 50. Means 50 have the structure described in FIG. 1. Subsequently, an analytical function-is fitted in, i.e. adjusted (60), using the incomplete contour line, as it were, as support locations for the contour profile of the tire, that is to say of the surface without any localized unevenness. The geometric anomaly of the surface, that is to say the side wobble of the tire, is then calculated from the amplitude of the fitted course of height. Using means 70 for comparing the amplitude of the analytical function to a threshold value, means 80 for discarding a tire if the amplitude is larger than a threshold value, are fed so as to decide either that the side wobble of the tire is such that a tire may still be used (branch 82), or that the tire has a side wobble larger than an admissible limit (branch 84).

Any function may be employed as an analytical function used by the means 60. However, a harmonic function is preferred, which may be a Fourier series, having a predetermined number of harmonic waves. The spatial frequency of the fundamental wave is equated with the inverses of the length of the incomplete contour line. The first harmonic wave then has double the frequency, the second harmonic wave has triple the frequency, etc. It shall be pointed out that any incomplete contour line may be adjusted using a Fourier series of any desired length. Thereby, the empty spaces of the incomplete complete contour line are filled up. Due to the recognition of whether or not a tire has a side wobble, however, the filled-up contour line is no longer used, but it is the maximum amplitude of the fitting function, which is an overlay of a certain number of Fourier harmonics, that is still used.

Alternatively, other base functions may also be used to represent the incomplete contour line by means of an analytic fitting function.

In the following, reference shall be made to FIG. 6 to show a further possibility of application of the incomplete contour line of the tire acquired in accordance with the invention. The apparatus, represented in FIG. 6, for characterizing localized unevenness on a surface again includes means for determining the incomplete contour line of the surface, that is to say, for example, of a tire 50. In contrast to adjusting an analytical function, as has been represented using FIG. 5, now the empty spaces are merely filled up (55) to obtain a filled-up contour line. This filling-up is effected using a known interpolation. For approximate decisions, a linear interpolation will suffice. However, improved interpolation will result, for example, from cubic splines, so that the filled-up contour line has a clear course.

Using means 65, the filled-up contour line is now subtracted from the original contour line, such that, with reference again to FIG. 3, the dashed line 30 results, which, however, still includes both the relief-like points of unevenness 22a, 22b and the bulge 21b and the constriction 21a. By subtracting the filled-up contour line from the original contour line, the side wobble, which was the feature of interest in the apparatus represented in FIG. 5, was therefore extracted.

If the tire is captured in a radial form rather than the peripheral contour line represented in FIG. 3, a radial contour line of the tire results which comprises both bulges and constrictions and writing. In this case, means 50, 55 and 65 of FIG. 6 serve to extract the doming of the tire from the originally captured contour line. The inventive concept may therefore be employed instead of band-pass filtering to achieve extraction of the doming of the tire in accordance with WO 00/25088.

Referring again to FIG. 6, a determination of the type and height of the unevenness is effected using a threshold value with the help of means 75 on the basis of the result of the subtraction performed in means 65. It shall be pointed out that the determination of the type of the localized unevenness, i.e. whether it is an inscription or a bulge, may be carried out, for example, using a simple threshold value method. The classification of the bulge and/or constriction, that is to say whether the bulge or constriction is so pronounced that the tire must be discarded, may simply be performed by a height threshold value comparison. Depending on same, means 80 will or will not call for a tire to be discarded.

Figure 5:
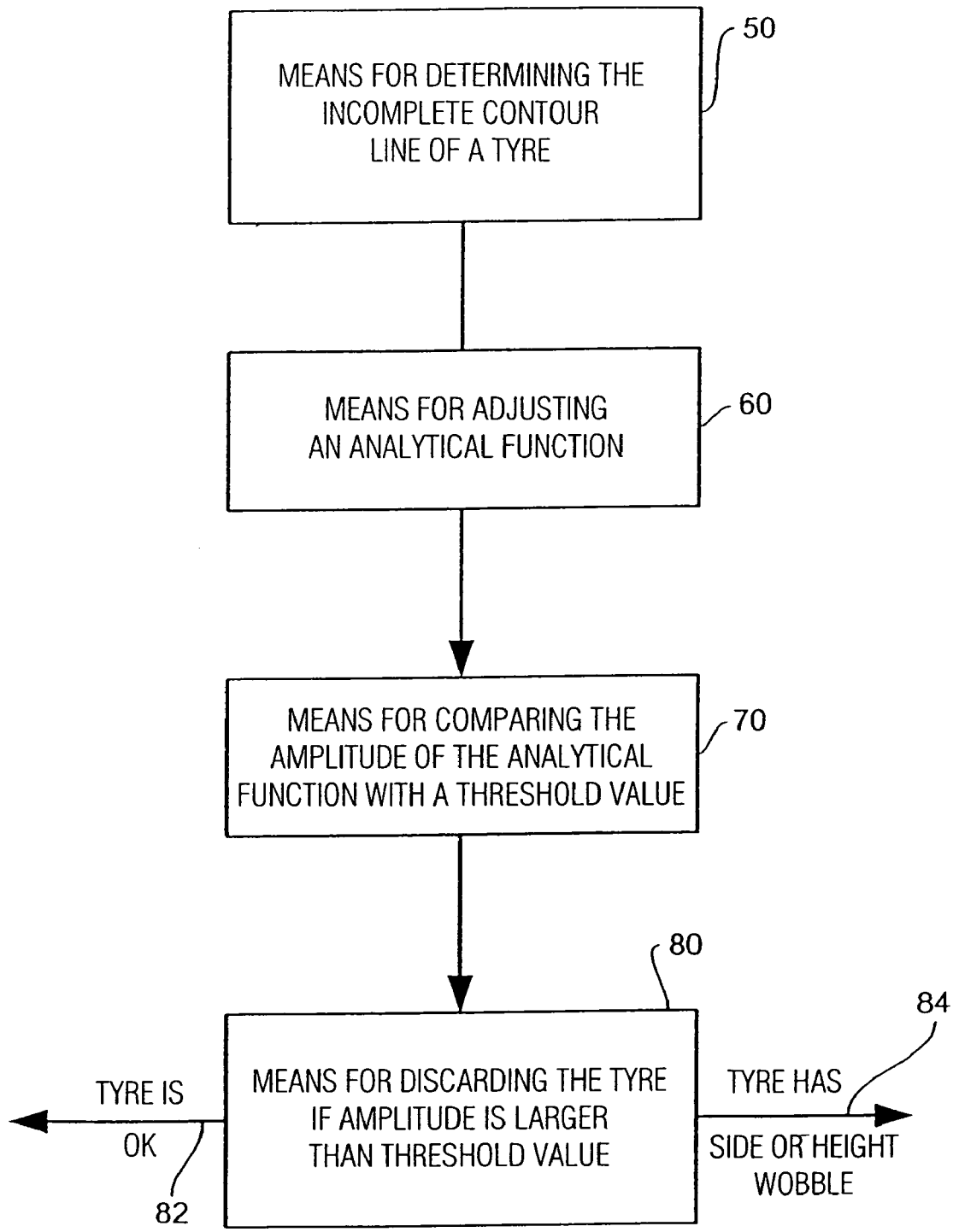
FIG. 5 shows a block-diagram representation of an inventive apparatus for determining a shape anomaly of a surface for using the incomplete contour line.
Figure 6:
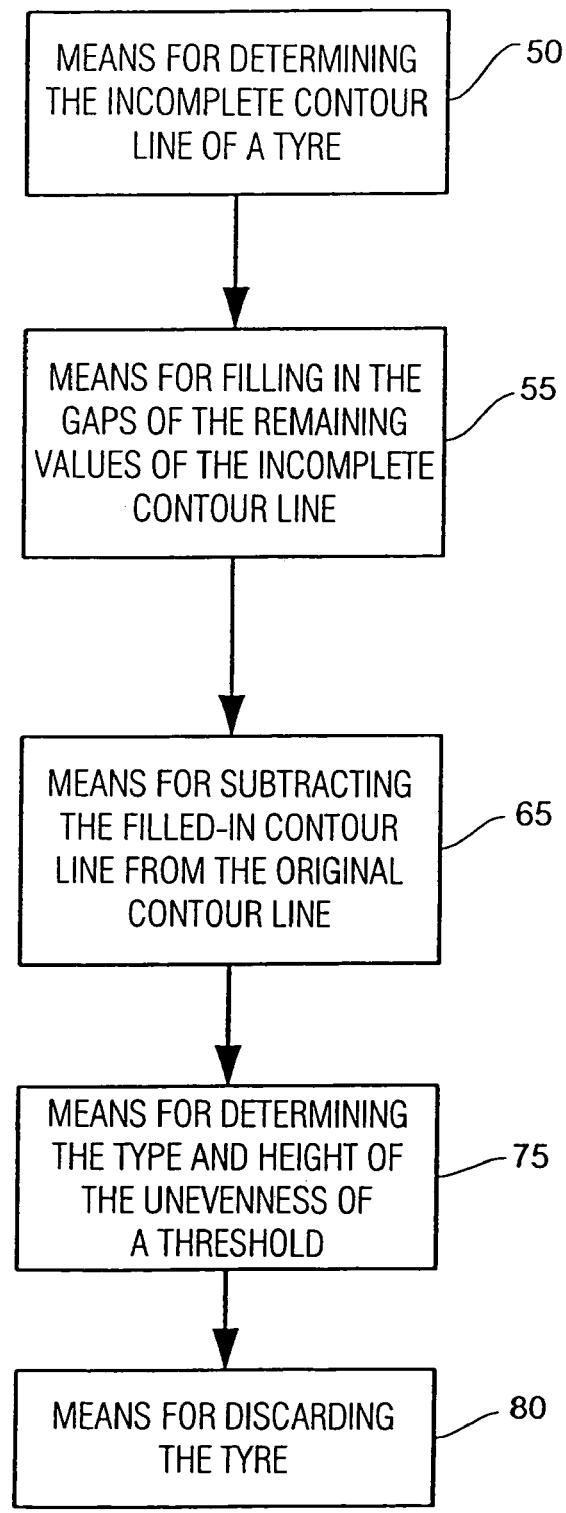
FIG. 6 shows a block-diagram representation of an inventive apparatus for characterizing a localized unevenness, wherein the incomplete contour line is used.

Generally speaking, the apparatuses represented in FIGS. 5 and 6 thus differ in that in FIG. 5, the localized points of unevenness have been eliminated to determine side wobble or height wobble of a tire, whereas in FIG. 6, it is the very side wobble or height wobble or a general doming of the surface that has been extracted to be able to classify the localized points of unevenness per se.

In accordance with a preferred embodiment of the present invention, use is made not only of one track in order to classify the tire, but of a plurality of tracks. Optionally, each track of the plurality of tracks which is to be measured may be processed separately. Alternatively, it is also possible to use a combination of several tracks to be measured and to average them so as to increase the reliability of measurement in accordance with the number of tracks averaged. Thus, the side wobble and/or the height wobble are obtained from the amplitude of the analytical fitting function obtained using means 60 of FIG. 5, either separately for each track or via the average of adjacent tracks, to improve the height resolution in accordance with the number of the tracks averaged in addition to increasing the reliability of the detection.

For determining the height wobble, that is to say of radial differences in height on the running tread, the incomplete contour line of the tire is used in a similar manner. In contrast to an inscription on the side face of the tire, a masking of locations is now performed wherein the profile of the tire has a depression, so that it is only the actual running tread of the tire that is used for determining the height wobble.

In the following, reference will be made to FIGS. 7a and 7b to represent a method for recognizing bulges/constrictions or, generally speaking, of essentially edgeless points of unevenness on and/or in a surface of a body, for example of a tire. Here, the bulges represent shape anomalies.

In a step 40, a data capture of the tire is carried out, it being possible to produce, to this end, an apparatus set forth above. Subsequently, a three-dimensional height image, for example of the tire side wall, is produced in a step 42. In a step 44, non-measurable regions are eliminated by means of interpolation between neighboring regions, and extreme height values are discarded to avoid artifacts. Extreme height values are created, for example, by measuring errors or by point-like excess rubber stocks which exist on new tires and, of course, do not present any problem with regard to the function or optics of the tire.

Subsequently, in a step 46, a reference height image is either provided externally by a database or is created using the body examined. The reference height image should be a reference height image of the object doming of as little structure as possible, which is preferably accomplished by one-dimensional long-range non-linear filtering via an adjustable object range (range of angles) in the tangential direction, i.e. in the circumferential direction, of the tire.

In a step 48, a even tire height image is subsequently created, wherein now only bulges (constrictions) and writing, but no side wobble and no doming exist. This is achieved by subtracting the reference representation from the three-dimensional representation of the body. To this end, use is made of the artifact-filtered three-dimensional height image, as is represented by an auxiliary arrow 50 in FIG. 7a. Eventually, a variation representation is calculated from the height representation created by step 48 (step 50). Subsequently, potential regions of defects are detected in a step 52. This is preferably accomplished by determining and combining regions in the height representation obtained by step 48, the regions combined being regions whose heights (represented by gray levels) are higher (or lower) than the detection threshold, and whose variations are below the variation threshold at the same time.

Optionally, these regions of defects may also be processed using a non-linear two-dimensional filter so as to eliminate artifacts and/or minor regions of defects as early as at this point. As potential regions of defects, regions are thus detected which raise relatively slowly from the tire and/or which sink into the tire relatively slowly, and which have a certain height. To provide orders of magnitude, it shall be pointed out that tires are examined sufficiently closely that even those bulges and/or constrictions are to be detected whose heights above the surfaces and/or whose depths below the surface is around 0.3 mm. Typically, bulges or constrictions whose heights and/or depths are 0.6 mm or more are considered critical. By means of the detection threshold used in step 52, the sensitivity of the detection may thus be set. If the detection threshold is set to be very high, only relatively few-potentially quality-impairing regions will be detected, whereas, if the detection threshold is set very low, a plurality of potentially quality-impairing defects are produced.

It shall be pointed out that the detection threshold may also be set to zero, so that the inventive concept degrades merely to a gradient and/or variation detection. Then all those regions of the surface of the tire which have a gradient below a specific value are detected. The potentially quality-impairing regions are then all those regions of the tire on which there is no writing and/or structuring having sharp edges. In this consideration it shall be assumed that regions of writing are not quality-impairing, whereas all other regions of the tire having a certain gradient may be quality-impairing. It shall be pointed out that even tire faces have no gradient, so that same are not detected as being potentially quality-impairing.

It shall be pointed out at this point that in step 52, the flow proceeds to region-by-region processing from a pixel-by-pixel processing which took place in the steps described before step 52. In a preferred embodiment of the present invention, there is no longer a pixel representation, in terms of data processing, at the output of step 52, but a list of potentially defective two-dimensional regions which, however, can be attributed without doubt to the original three-dimensional representation of the tires by means of their properties and coordinates.

At the end of the process, if one of the regions which is listed in the list of potentially quality-impairing regions, is classified as quality-impairing, it can thus be said at which location of the tire the quality impairment is located, so that a person performing manual quality control is immediately led to the problematic site on the tire.

Figure 7A:
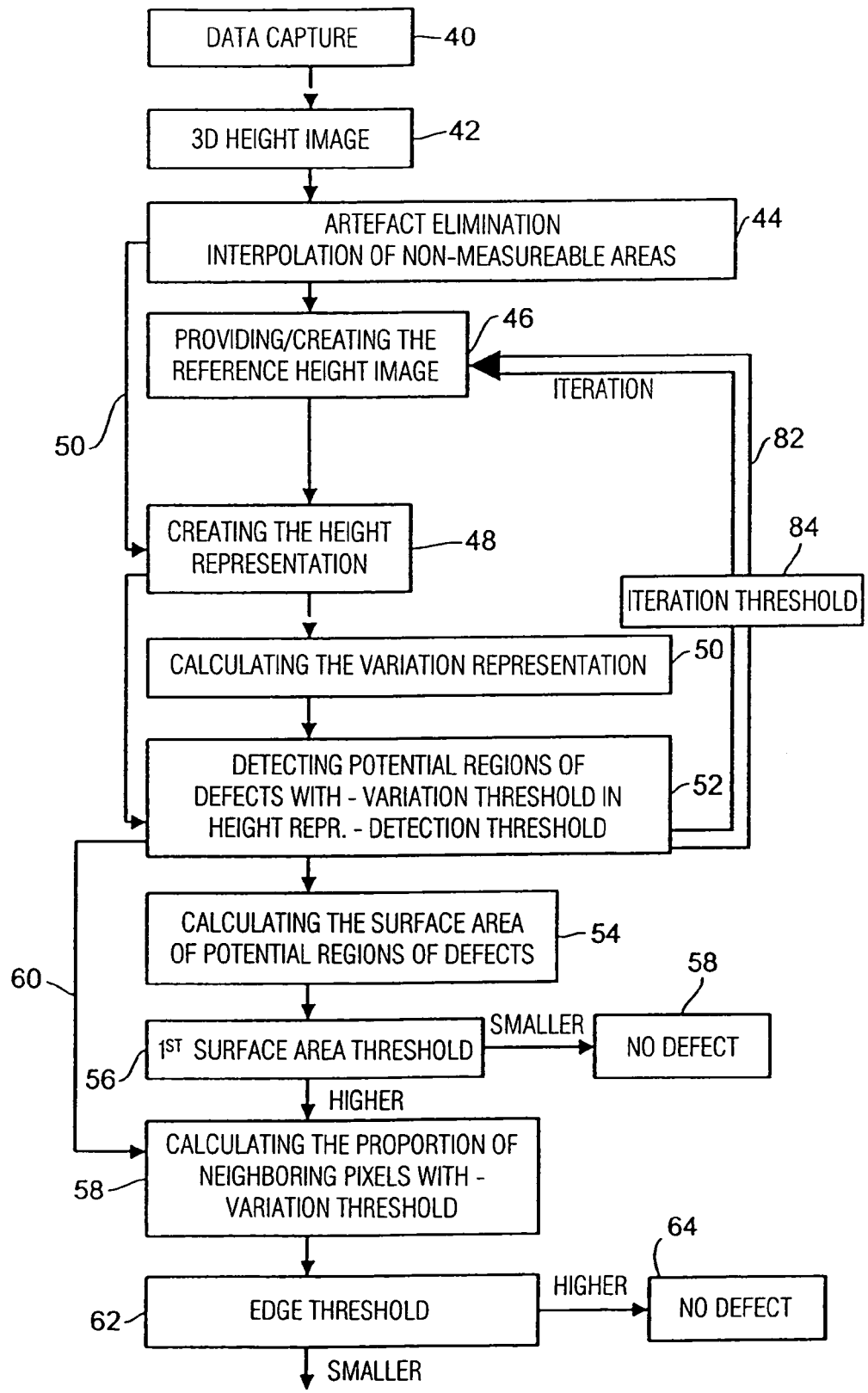
FIGS. 7a and 7b show a flow-chart representation for representing a two-dimensional method for detecting localized points of unevenness.
Figure 7B:
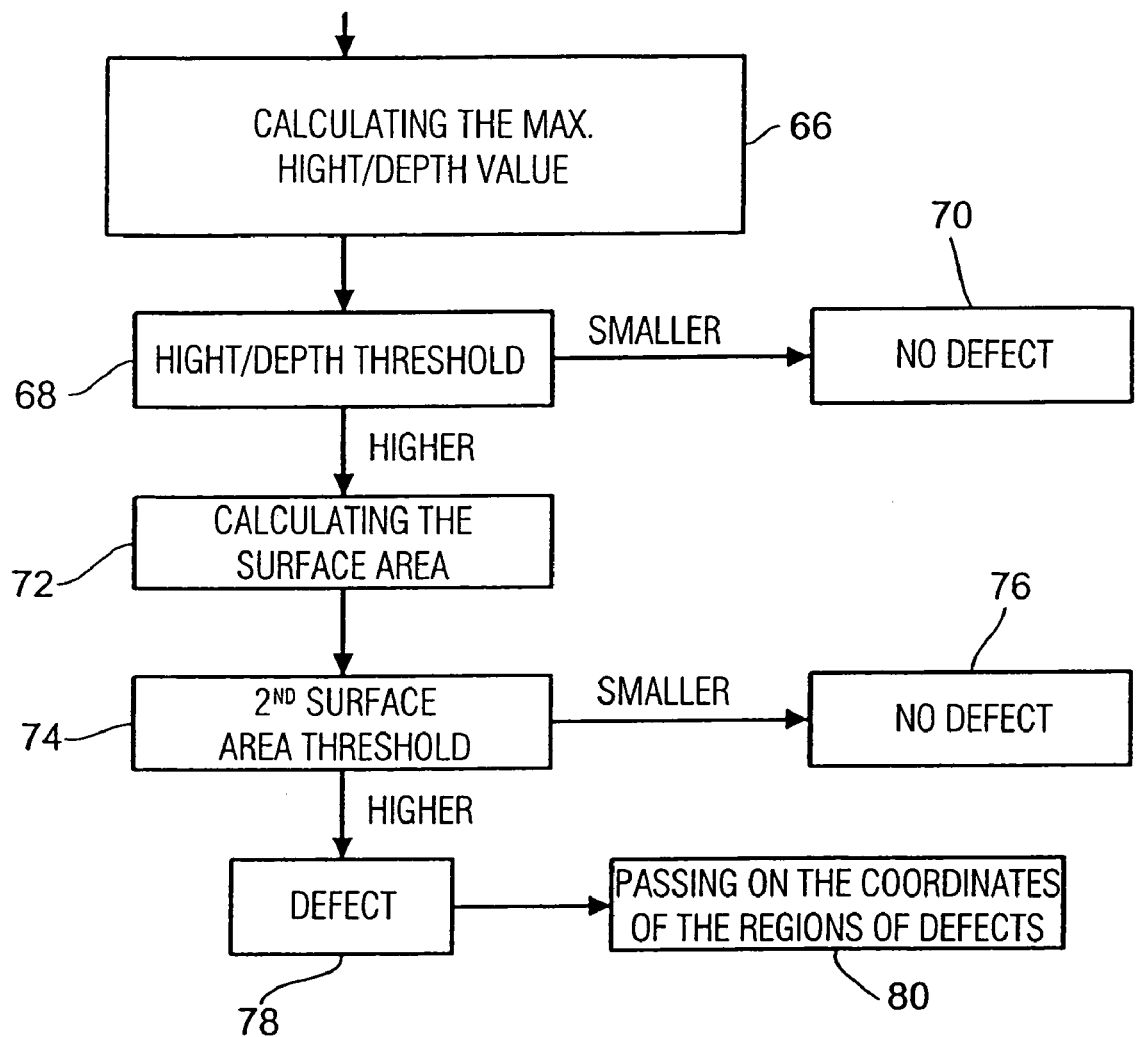

In the method shown in FIG. 7a, a calculation of the areas of the regions obtained by step 52, which are potential regions of defect, is performed in a step 54. In a step 56, the areas calculated are compared to a predetermined first area threshold. If it is found that the area of a potential region of defects is smaller than the area threshold itself, this means that this region of defects is uncritical due to its small extension, and that this potential region of defects thus does not comprise any defects (58).

However, if it is found that the area of a potential region of defects is larger than the area threshold, this region of defects will be retained in the first of potential regions of defect. However, the potential region of defect which has found to be unproblematic is eliminated from the list of potentially quality-impairing regions.

In a step 58, further examination of the remaining potential regions of defects is performed. In particular, the percentage of those neighboring pixels of the potential regions of defects either calculated in step 52 or remaining after step 56, which neighboring pixels have a high variation, i.e. a high gradient, is calculated. To this end, the variation representation of step 50 is used, as is shown by an arrow 60. For regions whose percentage of neighboring pixels with a high variation is above a so-called edge threshold (step 62) are nevertheless recognized as structuring, and classified as non-defective (64). However, if the percentage of the neighboring pixels of the region concerned is smaller than the predetermined edge threshold used in block 62, it may be assumed that there is no structure limited by edges here, and that the region concerned is still potentially quality-impairing.

The regions discarded by the comparison with the edge threshold in block 62 are, for example, such regions which do indeed have sharply delimited boundary but which are not fully flat within the boundary, that is to say which have a variation of zero, and which additionally have, within the sharp delimitation, a depression or elevation ascending gently and descending gently. Tire stampings may have such a structure. By examining the neighboring pixels of the region it may be ascertained whether there was a high variation immediately adjacent, so that, despite the fact that such a region has been classified as potentially defective in the examination in the means 52, same is still an uncritical target structuring. The percentage, that is to say the edge threshold, which becomes adjustable between 0 and 100%, will preferably be in a range between 80 and 100%, it being possible, however, to individually deal with the specific type of tire and/or the accuracy of the optical detection.

Of the remaining potential quality-impairing regions, the maximum height and/or depth value is calculated now in a step 66. Hereupon, a comparison operation of the values obtained with a height threshold or a depth threshold is performed in a block 68, it being possible for the height threshold and the depth threshold to have identical or different values, since the case may occur wherein bulges having a specific height are more critical than constrictions having the same height. If it is found out that the maximum height/depth of a region calculated has a higher value than the respective threshold, these respective regions are taken into account in further calculation. If it is found out, however, that the maximum heights/depths are smaller than the respective threshold, these regions are classified as undercritical. They do not present regions of defects (block 70), since, although they have passed some tests so far, their height/depth is too small for this unevenness to be critical in terms of the function of the tire and/or in terms of the function of the body undergoing a quality check by means of the surface examination.

Subsequently a calculation of the areas of the remaining regions is performed in a step 72, calculations of areas generally being performed by adding up the pixels in a region and then converting the magnification/reduction factors of the optics.

Eventually, the potentially quality-impairing regions which still remain after step 68 has been carried out, that is to say whose area has been calculated in step 72, are compared to a second area threshold, wherein, if their area value is smaller than the second area threshold, same are not classified as problematic, i.e. do not represent a defect (block 76), whereas, if it is determined, in block 74, that the area of this region is larger than the second area threshold, this region is eventually classified as a region of defects (block 78). As has already been mentioned, the coordinates and extension of the region of defects, or, if several regions are problematic, of these several regions of defects, may be output in a step 80 to make it possible for a manual recheck to quickly find the respective locations.

In accordance with the invention, the above method can be used to detect and eliminate any localized points of unevenness in a two-dimensional representation of the tire so as to obtain an incomplete height representation of the tire.

To this end, an iteration 82 may be performed by iteratively repeating steps 46, 48, 50, 52 after step 52, as is indicated by the iteration arrow 82. To do this, only those object ranges which are not potentially quality-impairing and which additionally are no regions of writing, i.e. which have a high gradient, are now used to provide/create the reference height image in steps 46. The remaining object ranges form the two-dimensional incomplete representation which, in the next iteration step, is interpolated and used so as to be able to measure bulges etc. even more reliably. In certain cases, however, the information about the regions which are potentially quality-impairing and which have edges, all of which may be detected in step 52, may suffice to determine the incomplete representation.

The incomplete three-dimensional representation which will remain, for example, of the tire, may be fitted and replaced by analytical (periodic or aperiodic) functions. Alternatively, the entire tire shape may be analytically fitted using the remaining object regions. Alternatively, interpolation may be used, for example, by means of cubic splines or similar methods.

The number of iterations to be performed depends on the measuring accuracy desired. A termination criterion may be defined, for example, such that the coefficients or the differences in the absolute height values of the domed tire shape from subsequent iterations differ by less than a certain threshold, as is represented schematically by a block 84 in FIG. 7a which is designated as "iteration threshold".

It shall be pointed out at this point that the order of the individual threshold value decisions is arbitrary. In addition, a single area threshold would, in principle, suffice. However, if two area thresholds are used (block 56 and block 74), intermediate results relating to the tire may also be obtained, specifically results as to whether it exhibits bulges and/or constrictions, and whether the bulges are under-critical, i.e. whether their area is between the first and second area thresholds. Of course, the area threshold decision may take place, for example, before the edge threshold decision or before the height threshold decision (block 68). To minimize the calculation expense, however, it is preferred to initially perform the decisions with which as large a number of the potentially quality-impairing regions as possible are classified as non-critical, so that the list of the potentially quality-impairing regions to be examined one after the other becomes as short as possible as fast as possible. Alternatively, the order of the threshold value decisions may be selected such that a defective region is found as fast as possible, which leads to the tire being discarded. In this case it is irrelevant whether any further defective regions exist and/or whether any further potentially defective regions exist, since one defective region suffices for the tire to become a defective tire.

What is claimed is:

1. Method for characterizing a surface (20) having a localized unevenness (21a, 21b, 22a, 22b), comprising:
    creating (10) a plurality of adjacent contour lines of the surface to create a two-dimensional height representation of the surface, a contour line of the surface being created as a function of a location variable ($\phi$);
    detecting (12) the localized unevenness (21a, 21b, 22a, 22b) in the two-dimensional height representation, wherein the step of detecting (12) comprises
        creating a variation representation from the height representation (50),
        detecting localized points of unevenness delimited by edges using a variation threshold, and
        detecting essentially edge-free localized points of unevenness using the variation threshold (52); and
    eliminating (14) the detected points of unevenness delimited by edges and the detected essentially edge-free points of unevenness from the height representation, so that an incomplete representation of the surface results which characterizes the surface without the localized unevenness.

2. Method as claimed in claim 1, wherein the localized unevenness is an edge-like relief structure (22a, 22b), and wherein the step of detecting (12) comprises:
    determining a first edge and an adjacent second edge of a contour line using a gradient of the contour line as a function of the location variable, the region between the first and second edges being the detected localized unevenness.

3. Method as claimed in claim 2, wherein the first and second edges are determined by the fact that the amount of the gradient of the contour line is higher than a predetermined threshold value.

4. Method as claimed in any one of the previous claims, wherein the localized unevenness is a bulge (21b) or a depression (21a) on and/or in the surface, and wherein the step of detecting (12) comprises:
    determining the extension of the bulge and/or constriction along the location variable;
    comparing the determined extension along the location variable with a predetermined threshold value;
    if the determined extension is larger than the predetermined threshold value, determining the bulge and/or depression as a detected localized unevenness.

5. Method as claimed in any one of claims 2 to 4, wherein the surface is a side flank (20) of a vehicle tire, and the contour line is a circumferential track of the side face, the location variable being an angle of rotation.

6. Method for determining a shape anomaly of a surface (20) having a localized unevenness which is not to be determined as a shape anomaly, comprising:
    characterizing (50) the surface as claimed in claim 1 to obtain an incomplete representation of the surface which comprises merely information relating to the shape anomaly, but no information relating to the localized unevenness;
    adjusting (62) an analytical function to the incomplete surface;
    comparing (70) a maximum of the analytical function to a predetermined threshold value;
    determining (80) a shape anomaly if the maximum exceeds the threshold value.

7. Method as claimed in claim 6, wherein the surface is torus-shaped, and a contour line is a track in the tangential direction of the torus-shaped surface;
    wherein the analytical function is a harmonic function comprising at least one sinusoidal function with the circumference of the incomplete contour line as a location period interval, the amplitude of the harmonic function equaling a difference between a local maximum and a mean value of the harmonic function.

8. Method as claimed in claim 6 or 7, wherein the harmonic function comprises a sum of sinusoidal functions whose frequencies are multiples of the frequency of the lowest-frequency sinusoidal function, the number of the sinusoidal functions being larger than zero and smaller than a predetermined maximum value.

9. Method as claimed in any one of claims 6 to 8, wherein the surface is the side face of the vehicle tire, and the shape anomaly is a side wobble of the tire.

10. Method as claimed in any one of claims 6 to 8, wherein the surface is the running tread of a vehicle tire, and the shape anomaly is a height wobble of the vehicle tire.

11. Method for characterizing a localized unevenness (21*a*, 21*b*, 22*a*, 22*b*) on a surface (20), comprising:
    characterizing the surface as claimed in claim 1 to obtain an incomplete representation of the surface comprising merely information relating to the shape anomaly, but no information relating to the localized unevenness;
    filling up (52) the incomplete representation using the values of the incomplete representation to obtain a filled-up representation;
    subtracting (65) the filled-up representation from the original representation to obtain a representation of points of unevenness including merely information relating to the localized unevenness;
    classifying (75) the unevenness on the basis of its extension, height and/or geometrical shape.

12. Method as claimed in claim 11, wherein the step of filling up (55) includes adjusting an analytical function to the incomplete contour line.

13. Method as claimed in claim 11, wherein the step of filling up (55) includes performing an interpolation of a first and/or higher order.

14. Apparatus for characterizing a surface (20) having a localized unevenness (21*a*, 21*b*, 22*a*, 22*b*), comprising:
    means for creating (10) a plurality of adjacent contour lines of the surface to create a two-dimensional height representation of the surface, a contour line of the surface being created as a function of a location variable (φ);
    means for detecting (12) the localized unevenness (21*a*, 21*b*, 22*a*, 22*b*) in the two-dimensional height representation, wherein the step of detecting (12) comprises creating a variation representation from the height representation (50),
    detecting localized points of unevenness delimited by edges using a variation threshold, and
    detecting essentially edge-free localized points of unevenness using the variation threshold (52); and
    means for eliminating (14) the detected points of unevenness delimited by edges and the detected essentially edge-free points of unevenness from the height representation, so that an incomplete representation of the surface results which characterizes the surface without the localized unevenness.

15. Apparatus for determining a shape anomaly of a surface having a localized unevenness which is not to be determined as a shape anomaly, comprising:
    means for characterizing (50) the surface as claimed in claim 1 to obtain an incomplete representation of the surface which comprises merely information relating to the shape anomaly, but no information relating to the localized unevenness;
    means for adjusting (62) an analytical function to the incomplete surface;
    means for comparing (70) a maximum of the analytical function to a predetermined threshold value;
    means for determining (80) a shape anomaly if the maximum exceeds the threshold value.

16. Apparatus for characterizing a localized unevenness (21*a*, 21*b*, 22*a*, 22*b*) on a surface (20), comprising:
    means for characterizing the surface as claimed in claim 1 to obtain an incomplete representation of the surface comprising merely information relating to the shape anomaly, but no information relating to the localized unevenness;
    means for filling up (52) the incomplete representation using the values of the incomplete representation to obtain a filled-up representation;
    means for subtracting (65) the filled-up representation from the original representation to obtain a representation of points of unevenness including merely information relating to the localized unevenness;
    means for classifying (75) the unevenness on the basis of its extension, height and/or geometrical shape.

* * * * *

UNITED STATES PATENT AND TRADEMARK OFFICE
CERTIFICATE OF CORRECTION

PATENT NO. : 7,012,701 B2  Page 1 of 1
DATED : March 14, 2006
INVENTOR(S) : Hassler et al.

It is certified that error appears in the above-identified patent and that said Letters Patent is hereby corrected as shown below:

<u>Title page,</u>
Item [54], Title, should read -- METHOD AND APPARATUS FOR CHARACTERIZING A SURFACE, AND METHOD AND APPARATUS FOR DETERMINING A SHAPE ANOMALY OF A SURFACE --.

Signed and Sealed this

Sixth Day of June, 2006

JON W. DUDAS
*Director of the United States Patent and Trademark Office*